(12) United States Patent
Angel et al.

(10) Patent No.: US 6,770,293 B2
(45) Date of Patent: Aug. 3, 2004

(54) SOFT CAPSULES COMPRISING POLYMERS OF VINYL ESTERS AND POLYETHERS, THE USE AND PRODUCTION THEREOF

(75) Inventors: Maximilian Angel, Schifferstadt (DE); Karl Kolter, Limburgerhof (DE); Axel Sanner, Frankenthal (DE); Michael Gotsche, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/805,239

(22) Filed: Mar. 14, 2001

(65) Prior Publication Data

US 2002/0119169 A1 Aug. 29, 2002

(30) Foreign Application Priority Data

Mar. 14, 2000 (DE) .......................................... 100 12 063

(51) Int. Cl.⁷ ................................................. A61K 9/48
(52) U.S. Cl. ...................................................... 424/451
(58) Field of Search ................................. 424/451, 400

(56) References Cited

U.S. PATENT DOCUMENTS

| | | | | |
|---|---|---|---|---|
| 3,984,494 A | * | 10/1976 | Harreus et al. ................ | 525/61 |
| 5,342,626 A | | 8/1994 | Winston, Jr. et al. ......... | 424/461 |
| 5,777,046 A | | 7/1998 | Boeckh et al. ............... | 525/444 |
| 5,965,651 A | * | 10/1999 | Ishii et al. .................... | 524/388 |
| 5,972,508 A | * | 10/1999 | Boeckh et al. ............ | 427/213.3 |
| 6,579,953 B1 | * | 6/2003 | Gotsche et al. ............. | 525/451 |

FOREIGN PATENT DOCUMENTS

| | | | | |
|---|---|---|---|---|
| CA | 2300281 | | 2/1999 | |
| DE | 1 077 430 | | 3/1960 | |
| DE | 1 081 229 | | 5/1960 | |
| DE | 1 094 457 | | 12/1960 | |
| DE | 23 63 853 | | 7/1975 | |
| EP | 743 962 | | 11/1996 | |
| GB | 922457 | * | 4/1963 | |
| GB | 922458 | | 4/1963 | |
| WO | WO 91/19487 | | 12/1991 | |
| WO | WO 97/35537 | | 10/1997 | |
| WO | WO 98/27151 | | 6/1998 | |
| WO | WO 9827151 A1 | * | 6/1998 | ............. C08L/1/26 |
| WO | WO 99/07347 | | 2/1999 | |
| WO | WO 99/40156 | | 8/1999 | |

OTHER PUBLICATIONS

Hard Capsules, Development and Technology, The Pharmaceutical Press, 1987, p. 1.*

* cited by examiner

Primary Examiner—Thurman K. Page
Assistant Examiner—Robert M. Joynes
(74) Attorney, Agent, or Firm—Keil & Weinkauf

(57) ABSTRACT

The present invention relates to soft capsules comprising
 (a) polymers prepared by polymerization of vinyl esters in the presence of polyethers
 (b) where appropriate structure-improving auxiliaries and
 (c) where appropriate other conventional constituents,
the use and production thereof.

25 Claims, No Drawings

SOFT CAPSULES COMPRISING POLYMERS OF VINYL ESTERS AND POLYETHERS, THE USE AND PRODUCTION THEREOF the present invention relates to soft capsules, for example for pharmaceutical applications, comprising polymers prepared by polymerization of vinyl esters in the presence of polyethers, and, where appropriate, in the presence of structure-improving auxiliaries and/or other conventional shell constituents, and to the use and production thereof.

Soft capsules are distinguished by the fact that the production of the shell and the filling take place virtually simultaneously in one stop. The shell of such capsules are often also referred to as soft gelatin, which is why the capsules are of ten also referred to as soft gelatin capsules. Since geltain is per se a brittle material of low flexibility, it must be plasticizers are low molecular weight compounds, ordinarily liquids such as, for example, glycerol, propylene glycol, polyethylene glycol 400. Such capsules often additionally contain dyes, opacifying agents and preservatives.

Although gelatin is frequently employed, it has numerous disadvantages. Thus, gelatin is a material of animal origin and thus not kosher. In addition, there is always a slight residual risk of BSE, because gelatin from cattle is preferably used to produce it. Obtaining suitable gelatin is very complicated and requires strict supervision of the process. Despite this, difference between batches are large because of the animal origin, which is subject to a certain variability. Gelatin is very susceptible to microbes because it represents a good nutrient medium for microorganisms. It is therefore necessary to take appropriate measures during the production as well as the use of such packing materials. The use of preservatives is frequently indispensible.

The plasticizers which are absolutely necessary to produce gelatin capsules frequently migrate from the shell into the filling and cause changes there. The shell loses plasticizers and becomes brittle and mechanically unstable during the course of storage. In addition, the shell of a soft gelatin capsule has a relatively high water content, which likewise has a plasticizing effect. On storage of such capsules with pure humidity there is evaporation of water from the shell, which likewise makes the capsule brittle. The same thing happens when very hygroscopic materials are encapsulated. Particularly hygroscopic or hydrolysis-sensitive substances cannot be encapsulated at all.

The rate of dissolution of gelatin is relatively slow. A higher rate of dissolution in gastric or intestinal fluid would be desirable for rapid release of active ingredients.

Numerous substances lead to interactions with gelatin, such as, for example, aldehydes, polyphenols, reducing sugars, multiply charged cations, electrolytes, cationic or anionic polymers etc., with crosslinking frequently occurring and the capsule then disintegrating or dissolving only very slowly or not at all. Such changes are catastrophic for a drug product because efficacy is lost. Many drugs also lead to interactions with gelatin. In some cases during storage there is formation of drug degradation products with, for example, an aldehyde structure, which lead to crosslinking of the gelatin. Since gelatin has both acidic and basic groups, it is clear that reactions easily occur with other charged molecules.

Gelatin can be cleaved by enzymes. Contamination by enzymes or bacteria which release enzymes may drastically alter the properties of gelatin.

Soft gelatin capsules very readily stick together under warm and moist conditions.

The adhesion of film coatings to soft gelatin capsules is extremely poor. For them it is frequently necessary first to apply a special subcoating, which is inconvenient.

Because of these many disadvantages, there has been no lack of attempts to replace gelatin wholly or partly in soft capsules.

For example, polyvinyl alcohol has been described for this purpose. However, polyvinyl alcohol has a slow rate of dissolution, likewise requires additional plasticizers, which in turn may migrate and which, as described above, may alter the properties of the filling, and it may moreover become extremely brittle as a consequence of internal crystallization. In particular, the flexibility decreases drastically during the course of storage if the ambient humidity is low.

U.S. Pat. No. 5,342,626 describes a combination of gellan, carrageenan and mannan for producing soft capsules or microcapsules. All these components are of natural origin and are subject to the natural variations in quality. Low molecular weight plasticizers are necessary and the products become brittle when the ambient humidity is low. Similar is true of the soft or hard capsules made of carrageenan which are described in the application WO 99/07347.

WO 91/19487 describes a combination of a cationic polymer and an anionic polymer. It is evident merely from the data given that the flexibility changes greatly with the ambient humidity; it decreases greatly when the humidity becomes less. This is understandable because the charges on the polymers greatly attract water. The line between polymer mixtures which are too tacky and too brittle is stated to be very narrow. The charges on the polymers may lead to interactions with the filling material and the drugs, especially since most drugs are likewise charged.

WO 99/40156 describes combinations of polyethylene glycols of various molecular weights which are suitable for producing films or soft capsules. However, polyethylene glycols with a high molecular weight dissolve only slowly in water and are brittle. Although combination with polyethylene glycols with a very low molecular weight makes them somewhat more flexible, they also become more tacky. In addition, they may in turn migrate into the filling because of their low molecular weight.

The application WO 98/27151 describes a mixture of cellulose ethers and polysaccharides plus sequestering agents, where the cellulose ether represents the main constituent (90 to 99.98%) for producing hard and soft capsules. Because of the brittleness of the cellulose ethers, this preparation is suitable without plasticizers at the most for hard gelatin capsules and, if plasticizers are added, the above-mentioned disadvantages reappear. The rate of dissolution of such capsules is likewise unsatisfactory.

DE-A2 2 363 853 describes the use of partially hydrolyzed copolymers of vinyl acetate on polyethylene glycol for producing hard capsules for medicines. There are no references in this publication to the use of the copolymers for producing soft capsules.

However, the requirements to be met by hard capsules are quite different from those for soft capsules. Hard capsules require great strength, while flexibility is a priority with soft capsules. The production processes also differ entirely. In the case of hard capsules, firstly only the shell is produced in 2 separate parts, a cap and a body, by a dip process, whereas in the case of soft capsules the shell and the filling are produced virtually simultaneously.

In the case of hard capsules, after production of cap and body these are loosely fitted together so that the pharmaceutical manufacturer is able to separate the two parts again mechanically, introduce his powder and close the capsule. Detailed examination of this processing makes it clear that the two capsule parts must be very mechanically stable, especially since the filling machines operate very rapidly and changes in shape would bring the entire process to a stop.

In the case of soft capsules, the shell must firstly be absolutely leakproof so that the filling, which is usually liquid, cannot escape, and secondly very flexible because the filling would otherwise escape through cracks or microfissures. Particularly high flexiblity is necessary for production because the polymer film is sucked into drilled cavities and is thus greatly deformed and stretched. The production of soft capsules is a technologically very demanding process, which is why the polymer properties and the machines must be harmonized and adjusted accurately.

The entirely different processes for producing hard and soft gelatin capsules are described in W. Fahrig and U. Hofer, Die Kapsel, Wissenschaftliche verlagsgesellschaft mbH Stuttgart, 1983, pp. 58–82.

DE 1 077 430 describes a process for producing graft copolymers of vinyl esters on polyalkylene glycols.

DE 1 094 457 and DE 1 081 229 describe processes for producing graft copolymers of polyvinyl alcohol on polyalkylene glycols by hydrolyzing the vinyl esters and the use thereof as protective colloids, water-soluble packaging films, as sizing and finishing agents for textiles and in cosmetics.

The application WO 97/35537 describes a special process for producing soft capsules using various materials, mainly polyvinyl alcohol. Before the encapsulation, a solvent is applied to the film to partly dissolve it so that better adhesion can be achieved. However, this is necessary only for films which are correspondingly difficult to process.

It is an object of the present invention to develop a material for soft capsules which is superior to gelatin and many substitute materials disclosed to date and, in particular, can be processed even without additional plasticizers.

We have found that this object is achieved by soft capsules comprising
a) polymers prepared by polymerization of vinyl esters in the presence of polyethers
b) where appropriate structure-improving auxiliaries and
c) where appropriate other conventional constituents.

The polymers (a) are obtainable by free-radical polymerization of
a) at least one vinyl ester in the presence of
b) polyether-containing compounds
and, where appropriate, one or more copolymerizable monomers c) and subsequent at least partial hydrolysis of the ester functions in the original monomers a). The soft capsules according to the invention are preferably used for producing pharmaceutical dosage forms.

During production of the polymers used according to the invention there may be during the polymerization a grafting onto the polyether-containing compounds (b), which may lead to the advantageous properties of the polymers. However, mechanisms other than grafting are also conceivable.

Depending on the degree of grafting, the polymers used according to the invention comprise both pure graft copolymers and mixtures of the abovementioned graft copolymers with ungrafted polyether-containing compounds and homo- or copolymers of monomers a) and c).

Polyether-containing compounds (b) which can be used are both polyalkylene oxides based on ethylene oxide, propylene oxide, butylene oxide and other alkylene oxides, and polyglycerol.

Depending on the nature of the monomer building blocks, the polymers contain the following structural units.

—(CH$_2$)$_2$—O—,  —(CH$_2$)$_3$—O—,  —(CH$_2$)$_4$—O—,
—CH$_2$—CH(R$^6$)—,  —CH$_2$—CHOR$^7$—CH$_2$—O—
with R$^6$ C$_1$–C$_{24}$-alkyl;
R$^7$ hydrogen, C$_1$–C$_{24}$-alkyl, R$^6$—C(=O)—, R$^6$—NH—C(=O)—.

It is moreover possible for the structural units to be both homopolymers and random copolymers and block copolymers.

The polyethers (b) preferably used are polymers of the general formula I

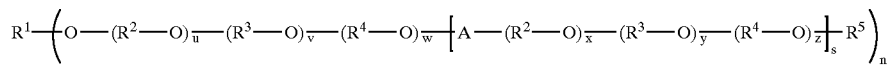

in which the variables have, independently of one another, the following meaning:

R$^1$ hydrogen, C$_1$–C$_{24}$-alkyl, R$^6$—C(=O)—, R$^6$—NH—C(=O)—, polyalcohol residue;

R$^5$ hydrogen, C$_1$–C$_{24}$-alkyl, R$^6$—C(=O)—, R$^6$—NH—C(=O)—;

R$^2$ to R$^4$ —(CH$_2$)$_2$—, —(CH$_2$)$_3$—, —(CH$_2$)$_4$—, —CH$_2$—CH(R$^6$)—, —CH$_2$—CHOR$^7$—CH$_2$—;

R$^6$ C$_1$–C$_{24}$-alkyl;

R$^7$ hydrogen, C$_1$–C$_{24}$-alkyl, R$^6$—C(=O)—, R$^6$—NH—C(=O)—;

A —C(=O)—O, —C(=O)—B—C(=O)—O, —C(=O)—NH—B—NH—C(=O)—O;

B —(CH$_2$)$_t$—, arylene, optionally substituted;

n 1 to 1000;
s 0 to 1000;
t 1 to 12;
u 1 to 5000;
v 0 to 5000;
w 0 to 5000;
x 0 to 5000;
y 0 to 5000;
z 0 to 5000.

The terminal primary hydroxyl groups of the polyethers produced on the basis of polyalkylene oxides, and the secondary OH groups of polyglycerol may moreover be present both free in unprotected form and etherified with alcohols with a C$_1$–C$_{24}$ chain length or esterified with carboxylic acids with a C$_1$–C$_{24}$ chain length, or reacted with isocyanates to give urethanes.

Alkyl radicals which may be mentioned for R$^1$ and R$^5$ to R$^7$ are branched or unbranched C$_1$–C$_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2- methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives of the abovementioned alkyl radicals which may be mentioned are branched or unbranched $C_1$–$C_{12}$–, particularly preferably $C_1$–$C_6$-alkyl chains.

The number average molecular weight of the polyethers is in the range below 1000000, preferably in the range from 300 to 100000, particularly preferably in the range from 500 to 50000, very particularly preferably in the range from 800 to 40000.

It is advantageous to use homopolymers of ethylene oxide or copolymers with an ethylene oxide content of from 40 to 99% by weight. Thus, the content of ethylene oxide units in the ethylene oxide polymers to be preferably employed is from 40 to 100 mol %. Suitable comonomers for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content of the copolymers is preferably from 40 to 99 mol %, the propylene oxide content is from 1 to 60 mol % and the content of butylene oxide in the copolymers is from 1 to 30 mol %. Not only straight-chain but also branched homo- or copolymers can be used as polyether-containing compouds b).

Branched polymers can be produced by, for example, adding ethylene oxide and, where appropriate, also propylene oxide and/or butylene oxides onto polyalcohol residues, for example onto pentaerythritol, glycerol or onto sugar alcohols such as D-sorbitol and D-mannitol, as well as polysaccharides such as cellulose and starch. The alkylene oxide units in the polymer may be randomly distributed or present in the form of blocks.

However, it is also possible to use polyesters of polyalkylene oxides and aliphatic or aromatic dicarboxylic acids, for example oxalic acid, succinic acid, adipic acid and terephthalic acid, with molecular weights of from 1500 to 25000 as described, for example, in EP-A-0 743 962, as polyether-containing compound. A further possibility is also to use polycarbonates through reaction of polyalkylene oxides with phosgene or carbonates such as, for example, diphenyl carbonate, and polyurethanes through reaction of polyalkylene oxides with aliphatic and aromatic diisocyanates.

Particularly preferred polyethers (b) are polymers of the general formula I with a number average molecular weight of from 300 to 100,000, in which the variables have, independently of one another, the following meaning:

$R^1$ hydrogen, $C_1$–$C_{12}$-alkyl, $R^6$—C(=O)—, $R^6$—NH—C(=O)—, polyalcohol residue;

$R^5$ hydrogen, $C_1$–$C_{12}$-alkyl, $R^6$—C(=O)—, $R^6$—NH—C(=O)—;

$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ $C_1$–$C_{12}$-alkyl;

$R^7$ hydrogen, $C_1$–$C_{12}$-alkyl, $R^6$—C(=O)—, $R^6$—NH—C(=O)—;

n 1 to 8;

s 0;

u 2 to 2000;

v 0 to 2000;

w 0 to 2000.

Very particularly preferred polyethers b) are polymers of the general formula I with a number average molecular weight of from 500 to 50000, in which the variables have, independently of one another, the following meaning:

$R^1$ hydrogen, $C_1$–$C_6$-alkyl, $R^6$—C(=O)—, $R^6$—NH—C(=O)—;

$R^5$ hydrogen, $C_1$–$C_6$-alkyl, $R^6$—C(=O)—, $R^6$—NH—C(=O)—;

$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ $C_1$–$C_6$-alkyl;

$R^7$ hydrogen, $C_1$–$C_6$-alkyl, $R^6$—C(=O)—, $R^6$—NH—C(=O)—;

n 1;

s 0;

u 5 to 1000;

v 0 to 1000;

w 0 to 1000.

Further polyethers (b) which can be used are homo- and copolymers of polyalkylene oxide-containing ethylenically unsaturated monomers such as, for example, polyalkylene oxide (meth)acrylates, polyalkylene oxide vinyl ethers, polyalkylene oxide-(meth)acrylamides, polyalkylene oxide-allylamides or polyalkylene oxide-vinylamides. It is, of course, also possible to employ copolymers of such monomers with other ethylenically unsaturated monomers.

The following monomers capable of free-radical polymerization may be mentioned as component a) for the polymerization in the presence on the polyethers b):

Vinyl esters of aliphatic, saturated or unsaturated $C_1$–$C_{24}$-carboxylic acids such as, for example, formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachidic acid, behenic acid, lignoceric acid, cerotic acid and melissic acid.

It is preferred to use vinyl esters of the abovementioned $C_1$–$C_{12}$-carboxylic acids, in particular of the $C_1$–$C_6$-carboxylic acids. Vinyl acetate is very particularly preferred.

It is, of course, also possible to copolymerize mixtures of the particular monomers from group a).

The vinyl esters (a) may also be employed in a mixture with one or more ethylenically unsaturated copolymerizable comonomers (c), in which case the proportion of these additional monomers should be restricted to a maximum of 50% by weight. Proportions of 0 and 20% by weight are preferred. The term ethylenically unsaturated means that the monomers have at least one carbon-carbon double bond which is capable of free-radical polymerization and which may be mono-, di-, tri- or tetrasubstituted.

The preferred additionally employed ethylenically unsaturated comonomers (c) can be described by the following general formula:

where

X is selected from the group of radicals —OH, —OM, —OR$^{16}$, NH$_2$, —NHR$^{16}$, N(R$^{16}$)$_2$;

M is a cation selected from the group consisting of: Na$^+$, K$^+$, Mg$^{++}$, Ca$^{++}$, Zn$^{++}$, NH$_4^+$, alkylammonium, dialkylammonium, trialkylammonium and tetraalkylammonium;

the $R^{16}$ radicals can be identical or different and selected from the group consisting of —H, linear or branched-chain $C_1$–$C_{40}$-alkyl radicals, N,N-dimethylaminoethyl, 2-hydroxyethyl, 2-methoxyethyl, 2-ethoxyethyl, hydroxypropyl, methoxypropyl or ethoxypropyl.

$R^{15}$ and $R^{14}$ are, independently of one another, selected from the group consisting of: —H, linear or branched-chain $C_1$–$C_8$-alkyl chains, methoxy, ethoxy, 2-hydroxyethoxy, 2-methoxyethoxy and 2-ethoxyethyl.

Representative but non-limiting examples of suitable monomers (c) are, for example, acrylic acid or methacrylic acid and their salts, esters and amides. The salts may be derived from any nontoxic metal, ammonium or substituted ammonium counter ions.

The esters may be derived from linear $C_1$–$C_{40}$, branched-chain $C_3$–$C_{40}$ or carbocyclic $C_3$–$C_{40}$ alcohols, from polyfunctional alcohols with 2 to about 8 hydroxyl groups, such as ethylene glycol, hexylene glycol, glycerol and 1,2,6-hexanetriol, from amino alcohols or from alcohol ethers such as methoxyethanol and ethoxyethanol, (alkyl) polyethylene glycols, (alkyl)polypropylene glycols or ethoxylated fatty alcohols, for example $C_{12}$–$C_{24}$-fatty alcohols reacted with 1 to 200 ethylene oxide units.

Also suitable are N,N-dialkylaminoalkyl acrylates and methacrylates and N,N-dialkylaminoalkylacrylamides and methacrylamides of the general formula (III)

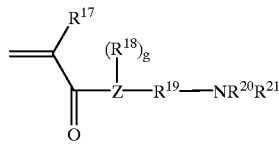

(III)

with $R^{17}$=H, alkyl with 1 to 8 C atoms, $R^{18}$=H, methyl, $R^{19}$=alkylene with 1 to 24 C atoms, optionally substituted by alkyl, $R^{20}$, $R^{21}$=$C_1$–$C_{40}$-alkyl radical, Z=nitrogen for g=1 or oxygen for g=0.

The amides may be unsubstituted, N-alkyl- or N-alkylamino-monosubstituted or N,N-dialkyl-substituted or N,N-dialkylamino-disubstituted, in which the alkyl or alkylamino groups are derived from linear $C_1$–$C_{40}$, branched-chain $C_3$–$C_{40}$ or carbocyclic $C_3$–$C_{40}$ units. The alkylamino groups may additionally be quaternized.

Preferred comonomers of formula III are N,N-dimethylaminomethyl (meth)acrylate, N,N-diethylaminoethyl (meth)acrylate, N,N-dimethylaminoethyl (meth)acrylate, N,N-diethylaminoethyl (meth)acrylate, N-[3-(dimethylamino)propyl]methacrylamide and N-[3-(dimethylamino)propyl]acrylamide.

Comonomers (c) which can likewise be used are substituted acrylic acids and salts, esters and amides thereof, where the substituents are located on the carbon atoms in position two or three of the acrylic acid, and are selected, independently of one another, from the group consisting of $C_1$–$C_4$-alkyl, CN, COOH, particularly preferably methacrylic acid, ethacrylic acid and 3-cyanoacrylic acid. These salts, esters and amides of these substituted acrylic acids may be selected as described above for the salts, esters and amides of acrylic acid.

Other suitable comonomers (c) are allyl esters of linear $C_1$–$C_{40}$, branched-chain $C_3$–$C_{40}$ or carbocyclic $C_3$–$C_{40}$ carboxylic acids, vinyl or allyl halides, preferably vinyl chloride and allyl chloride, vinyl ethers, preferably methyl, ethyl, butyl or dodecyl vinyl ether, vinylformamide, vinylmethylacetamide, vinylamine; vinyllactams, preferably vinylpyrrolidone and vinylcaprolactam, vinyl- or allyl-substituted heterocyclic compounds, preferably vinylpyridine, vinyloxazoline and allylpyridine.

Also suitable are N-vinylimidazoles of the general formula IV in which $R^{22}$ to $R^{24}$ are, independently of one another, hydrogen, $C_1$–$C_4$-alkyl or phenyl:

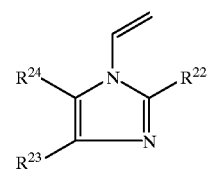

(IV)

Further suitable comonomers (c) are diallylamines of the general formula (V)

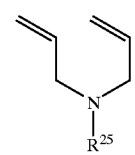

(V)

with $R^{25}$=$C_1$- to $C_{24}$-alkyl.

Further suitable comonomers (c) are vinylidene chloride; and hydrocarbons having at least one carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers.

Particularly suitable comonomers (c) are acrylic acid, methacrylic acid, ethacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl (meth) acrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth) acrylates, unsaturated sulfonic acids such as, for example, acrylamidopropanesulfonic acid;

acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylvinylimidazole, N,N-dimethylaminomethyl (meth)acrylate, N,N-diethylaminomethyl (meth) acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(diethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide;

maleic acid, fumaric acid, maleic anhydride and its monoesters, crotonic acid, itaconic acid, diallyldimethylammonium chloride, vinyl ethers (for example: methyl, ethyl, butyl or dodecyl vinyl ether), vinylformamide, vinylmethylacetamide, vinylamine; methyl vinyl ketone, maleimide, vinylpyridine, vinylimidazole, vinylfuran, styrene, styrenesulfonate, allyl alcohol, and mixtures thereof.

Of these, particular preference is given to acrylic acid, methacrylic acid, maleic acid, fumaric acid, crotonic acid, maleic anhydride and its monoesters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylates, 2-hydroxyethyl methacrylate, hydroxypropyl methacrylates, alkylene glycol (meth)acrylates, styrene, unsaturated sulfonic acids such as, for example, acrylamidopropanesulfonic acid, vinylpyrrolidone, vinylcaprolactam, vinyl ethers (for example: methyl, ethyl, butyl or dodecyl vinyl ether), vinylformamide, vinylmethylacetamide, vinylamine, 1-vinylimidazole, 1-vinyl-2-methylimidazole, N,N-dimethylaminomethyl methacrylate and N-[3-(dimethylamino) propyl]methacrylamide; 3-methyl-1-vinylimidazolium chloride, 3-methyl-1-vinylimidazolium methyl sulfate, N,N-dimethylaminoethyl methacrylate, N-[3-(dimethylamino)propyl]methacrylamide quaternized with methyl chloride, methyl sulfate or diethyl sulfate.

Monomers with a basic nitrogen atom may moreover be quaternized in the following way:

Suitable for quaternizing the amines are, for example, alkyl halides with 1 to 24 C atoms in the alkyl group, for example methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Further suitable quaternizing agents are dialkyl sulfates, in particular dimethyl sulfate or diethyl sulfate. The quaternization of the basic amines can also be carried out with alkylene oxides such as ethylene oxide or propylene oxide in the presence of acids. Preferred quaternizing agents are: methyl chloride, dimethyl sulfate or diethyl sulfate.

The quaternization can be carried out before the polymerization or after the polymerization.

It is additionally possible to employ the products of the reaction of unsaturated acids, such as, for example, acrylic acid or methacrylic acid, with a quaternized epichlorohydrin of the general formula (VI) ($R^{26}$=$C_1$- to $C_{40}$-alkyl).

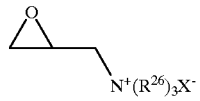

(VI)

Examples thereof are:
(meth)acryloyloxyhydroxypropyltrimethylammonium chloride and
(meth)acryloyloxyhydroxypropyltriethylammonium chloride.

The basic monomers can also be cationized by neutralizing them with mineral acids such as, for example, sulfuric acid, hydrochloric acid, hydrobromic acid, hydroiodic acid, phosphoric acid or nitric acid, or with organic acids such as, for example, formic acid, acetic acid, lactic acid or citric acid.

In addition to the abovementioned comonomers, it is possible to employ as comonomers (c) so-called macromonomers such as, for example, silicone-containing macromonomers with one or more groups capable of free-radical polymerization, or alkyloxazoline macromonomers as described, for example, in EP 408 311.

It is further possible to employ fluorine-containing monomers as described, for example, in EP 558423, and compounds which have a crosslinking action or regulate the molecular weight, in combination or alone.

Regulators which can be used are the usual compounds known to the skilled worker, such as, for example, sulfur compounds (e.g.: mercaptoethanol, 2-ethylhexyl thioglycolate, thioglycolic acid or dodecyl mercaptan), and tribromochloromethane or other compounds which have a regulating effect on the molecular weight of the resulting polymers.

It is also possible where appropriate to employ thiol-containing silicone compounds.

Silicone-free regulators are preferably employed.

It is also possible to employ crosslinking monomers as additional monomers c). The term crosslinking means that the monomers have at least two unconjugated ethylenic double bonds. Examples of suitable compounds are esters of ethylenically unsaturated carboxylic acids such as acrylic acid or methacrylic acid and polyhydric alcohols, ethers of at least dihydric alcohols, such as, for example, vinyl ethers or allyl ethers.

Examples of the underlying alcohols are dihydric alcohols such as 1,2-ethanediol, 1,2-propanediol, 1,3-propanediol, 1,2-butanediol, 1,3-butanediol, 2,3-butanediol, 1,4-butanediol, 2-butene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis (hydroxymethyl)cyclohexane, hydroxypivalic acid neopentyl glycol monoester, 2,2-bis(4-hydroxyphenyl) propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiapentane-1,5-diol, and polyethylene glycols, polypropylene glycols and polytetrahydrofurans with molecular weights of, in each case, from 200 to 10 000. Apart from the homopolymers of ethylene oxide or propylene oxide, it is also possible to employ block copolymers of ethylene oxide or propylene oxide or copolymers containing incorporated ethylene oxide and propylene oxide groups.

Examples of underlying alcohols with more than two OH groups are trimethylolpropane, glycerol, pentaerythritol, 1,2,5-pentanetriol, 1,2,6-hexanetriol, triethoxycyanuric acid, sorbitan, sugars such as sucrose, glucose, mannose. It is, of course, also possible for the polyhydric alcohols to be employed after reaction with ethylene oxide or propylene oxide as the corresponding ethoxylates or propoxylates. The polyhydric alcohols can also be firstly converted into the corresponding glycidyl ethers by reaction with epichlorohydrin.

Further suitable crosslinkers are the vinyl esters or the esters of monohydric unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, the monohydric unsaturated alcohols can also be esterified with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the polyhydric alcohols described above, for example of oleic acid, crotonic acid, cinnamic acid or 10-undecenoic acid.

Also suitable are straight-chain or branched, linear or cyclic aliphatic or aromatic hydrocarbons which have at least two double bonds which, in the case of the aliphatic hydrocarbons, must not be conjugated, for example divinylbenzene, divinyltoluene, 1,7-octadiene, 1,9-decadiene, 4-vinyl-1-cyclohexene, trivinylcyclohexane or polybutadienes with molecular weights of from 200 to 20000.

Also suitable are amides of unsaturated carboxylic acids such as, for example, acrylic and methacrylic acids, itaconic acid, maleic acid, and N-allylamines of at least difunctional amines, such as, for example, diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides from allylamine and unsaturated carboxylic acids such as acrylic acid, methacrylic acid, itaconic acid, maleic acid, or at least dibasic carboxylic acids like those described above.

Further suitable crosslinkers are triallylamine or corresponding ammonium salts, for example triallylmethylammonium chloride or methyl sulfate.

It is further possible to employ N-vinyl compounds of urea derivatives, at least difunctional amides, cyanurates or urethanes, for example of urea, ethyleneurea, propyleneurea or tartaramide, for example N,N'-divinylethyleneurea or N,N'-divinylpropyleneurea.

Further suitable crosslinkers are divinyldioxane, tetraallylsilane and tetravinylsilane.

Examples of particularly preferred crosslinkers are methylenebisacrylamide, divinylbenzene, triallylamine and triallylammonium salts, divinylimidazole, N,N'-divinylethyleneurea, products of the reaction of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin, and allyl or vinyl ethers of polyhydric alcohols, for example 1,2-ethanediol, 1,4-butanediol, diethylene glycol, trimethylolpropane, glycerol, pentaerythritol, sorbitan and sugars such as sucrose, glucose, mannose.

Very particularly preferred crosslinkers are pentaerythritol triallyl ether, allyl ethers of sugars such as sucrose, glucose, mannose, divinylbenzene, methylenebisacrylamide, N,N'-divinylethyleneurea, and (meth)acrylic esters of glycol, butanediol, trimethylolpropane or glycerol or (meth)acrylic esters of glycol, butanediol, trimethylolpropane or glycerol reacted with ethylene oxide and/or epichlorohydrin.

The proportion of the monomers with a crosslinking action is from 0 to 10% by weight, preferably 0 to 5% by weight, very particularly preferably 0 to 2% by weight.

The comonomers (c) according to the invention can, if they contain ionizable groups, be partly or completely neutralized with acids or bases before or after the polymerization, in order, for example, in this way to adjust the solubility or dispersibility in water to a desired extent.

Neutralizing agents which can be used for monomers with acidic groups are, for example, mineral bases such as sodium carbonate, alkali metal hydroxides, and ammonia, organic bases such as amino alcohols, specifically 2-amino-2-methyl-1-propanol, monoethanolamine, diethanolamine, triethanolamine, triisopropanolamine, tri(2-hydroxy-1-propyl)amine, 2-amino-2-methyl-1,3-propanediol, 2-amino-2-hydroxymethyl-1,3-propanediol, and diamines such as, for example, lysine.

To prepare the polymers, the monomers of component a) can be polymerized in the presence of the polyethers both with the aid of free radical-forming initiators and by exposure to high-energy radiation, which is intended to include the exposure to high-energy electrons.

The initiators which can be employed for the free-radical polymerization are the peroxo and/or azo compounds customary for this purpose, for example alkali metal or ammonium peroxodisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbonate, bis(o-toluyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane) dihydrochloride or 2,2'-azobis(2-methylbutyronitrile). Also suitable are indicator mixtures of redox initiator systems such as, for example, ascorbic acid/iron(II) sulfate/sodium peroxodisulfate, tert-butyl hydroperoxide/sodium disulfite, tert-butyl hydroperoxide/sodium hydroxymethanesulfinate.

Organic peroxides are preferably employed.

The amounts of initiator or initiator mixtures used based on monomer employed are between 0.01 and 10% by weight, preferably between 0.1 and 5% by weight.

The polymerization takes place at a temperature in the range from 40 to 200° C., preferably in the range from 50 to 140° C., particularly preferably in the range from 60 to 110° C. It is normally carried out under atmospheric pressure, but can also take place under reduced or elevated pressure, preferably between 1 and 5 bar.

The polymerization can be carried out, for example, as solution polymerization, bulk polymerization, emulsion polymerization, inverse emulsion polymerization, suspension polymerization, inverse suspension polymerization or precipitation polymerization without the methods which can be used being restricted thereto.

The procedure for bulk polymerization can be such that the polyether-containing compound b) is dissolved in at least one monomer of group a) and, where appropriate, one or more comonomers of group c) and, after addition of a polymerization initiator, the mixture is completely polymerized. The polymerization can also be carried out semicontinuously by initially introducing part, for example 10% of the mixture of the polyether-containing compound b), at least one monomer of group a), where appropriate one or more comonomers of group c) and initiator, heating the mixture to the polymerization temperature and, after the polymerization has started, adding the remainder of the mixture to be polymerized in accordance with the progress of the polymerization. The polymers can also be obtained by introducing the polyether-containing compounds of group b) into a reactor and heating to the polymerization temperature, and adding at least one monomer of group a), where appropriate one or more comonomers of group c) and polymerization initiator, either all at once, batchwise or, preferably, continuously, and polymerizing.

If required, the polymerization described above can also be carried out in a solvent. Examples of suitable solvents are alcohols such as methanol, ethanol, n-propanol, isopropanol, n-butanol, sec-butanol, tert-butanol, n-hexanol and cyclohexanol, and glycols such as ethylene glycol, propylene glycol and butylene glycol, and the methyl or ethyl ethers of the dihydric alcohols, diethylene glycol, triethylene glycol, glycerol and dioxane. The polymerization can also be carried out in water as solvent. In this case, a solution is initially present, which is more or less soluble in water depending on the amount of the added monomers of component a). In order to dissolve water-insoluble products which may be produced during the polymerization it is possible, for example, to add organic solvents such as monohydric alcohols with 1 to 3 carbon atoms, acetone or dimethylformamide. However, the procedure for the polymerization in water can also be such that the water-insoluble polymers are converted into a fine-particle dispersion by adding conventional emulsifiers or protective colloids, for example polyvinyl alcohol.

Examples of emulsifiers used are ionic or nonionic surfactants whose HLB is in the range from 3 to 13. For the definition of the HLB, reference is made to the publication by W. C. Griffin, J. Soc. Cosmetic Chem., volume 5, 249 (1954).

The amount of surfactants is from 0.1 to 10 by weight, based on the polymer. Use of water as solvent results in solutions or dispersions of the polymers. If solutions of the polymer are prepared in an organic solvent or in mixtures of an organic solvent and water, then from 5 to 2000, preferably 10 to 500, parts by weight of the organic solvent or mixture of solvents are used per 100 parts by weight of the polymer.

Preferred polymers are obtainable by free-radical polymerization of
a) 10 to 98% by weight of at least one vinyl ester of $C_1$–$C_{24}$-carboxylic acids in the presence of
b) 2 to 90% by weight of at least one polyether-containing compound and
c) 0 to 50% by weight of one or more other copolymerizable monomers.

Particularly preferred polymers are obtainable by free-radical polymerization of
a) 50 to 97% by weight of at least one vinyl ester of $C_1$–$C_{24}$-carboxylic acids in the presence of
b) 3 to 50% by weight of at least one polyether-containing compound and
c) 0 to 20% by weight of one or more other copolymerizable monomers.

Very particularly preferred polymers are obtainable by free-radical polymerization of
a) 65 to 97% by weight of at least one vinyl ester of $C_1$–$C_{24}$-carboxylic acids in the presence of
b) 3 to 35% by weight of at least one polyether-containing compound and
c) 0 to 20% by weight of one or more other copolymerizable monomers.

To prepare the polymers used according to the invention, the ester groups of the original monomers a) and, where appropriate, other monomers are cleaved after the polymerization by hydrolysis, alcoholysis or aminolysis. This process step is generally referred to as hydrolyis hereinafter. The hydrolysis takes place in a manner known per se by adding a base, preferably by adding a sodium or potassium hydroxide solution in water and/or alcohol. Methanolic sodium or potassium hydroxide solutions are particularly preferably employed. The hydrolysis is carried out at temperatures in the range from 10 to 80° C., preferably in the range from 20 to 60° C. The degree of hydrolysis depends on the amount of base employed, on the hydrolysis temperature, the hydrolysis time and the water content of the solution.

The degree of hydrolysis of the polyvinyl ester groups is in the range from 1 to 100%, preferably in the range from 40 to 100%, particularly preferably in the range from 65 to 100%, very particularly preferably in the range from 80 to 100%.

The polymers prepared in this way can be subsequently cationized by reacting hyydroxyl and/or amino functions present in the polymer with epoxides of the formula VI ($R^{26}$=$C_1$- to $C_{40}$-alkyl).

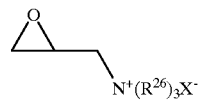

(VI)

It is possible and preferred for the hydroxyl groups of the polyvinyl alcohol units and vinylamine units produced by hydrolysis of vinylformamide to be reacted with the epoxides.

The epoxides of the formula VI can also be generated in situ by reacting the corresponding chlorohydrins with bases, for example sodium hydroxide.

2,3-Epoxypropyltrimethylammonium chloride or 3-chloro-2-hydroxypropyltrimethylammonium chloride is preferably employed.

The K values of the polymers should be in the range from 10 to 300, preferably 25 to 250, particularly preferably 25 to 200, very particularly preferably in the range from 30 to 150. The K value required in each case can be adjusted in a manner known per se by the composition of the starting materials. The K values are determined by the method of Fikentscher, Cellulosechemie, Vol. 13, pp. 58 to 64 and 71 to 74 (1932) in N-methylpyrrolidone at 25° C. and polymer concentrations which are between 0.1% by weight and 5% by weight, depending on the K value range.

After the hydrolysis, the polymer solutions can be steam distilled to remove solvents. The steam distillation results in aqueous solutions or dispersions, depending on the degree of hydrolysis and nature of the polyethers b), of the vinyl esters a) and of the possibly employed monomers c).

The resulting polymers can also be subsequently crosslinked by reacting the hydroxyl groups or amino groups in the polymer with at least bifunctional reagents. Water-soluble products are obtained with low degrees of crosslinking, while water-swellable or insoluble products are obtained with high degrees of crosslinking.

The polymers according to the invention can be reacted, for example, with dialdehydes and diketones, for example glyoxal, glutaraldehyde, succinaldehyde or terephthalaldehyde. Also suitable are aliphatic or aromatic carboxylic acids, for example maleic acid, oxalic acid, malonic acid, succinic acid or citric acid, or carboxylic acid derivatives such as carboxylic esters or anhydrides or carbonyl halides. Polyfunctional epoxides are also suitable, for example epichlorohydrin, glycidyl methacrylate, ethylene glycol diglycidyl ether, 1,4-butanediol diglycidyl ether or 1,4-bis(glycidyloxy)benzene. Also suitable are diisocyanates, for example hexamethylene diisocyanate, isophorone diisocyanate, methylenediphenyl diisocyanate, tolylene diisocyanate or divinyl sulfone.

Additionally suitable are inorganic compounds such as boric acid or boric acid salts, for example sodium metaborate, borax (disodium tetraborate), and salts of multiply charged cations, for example copper(II) salts such as copper(II) acetate or zinc, aluminum or titanium salts.

Boric acid or boric acid salts such as sodium metaborate or disodium tetraborate are suitable and preferred for the subsequent crosslinking. This may entail adding the boric acid or boric acid salts, preferably as salt solutions, to the solutions of the polymers according to the invention. The boric acid or boric acid salts are preferably added to the aqueous polymer solutions.

The boric acid or boric acid salts can be added to the polymer solutions immediately after preparation. However, it is also possible for the boric acid or boric acid salts to be added subsequently to the polymers according to the invention or during the soft capsule production process.

The proportion of boric acid or boric acid salts based on the polymers according to the invention is from 0 to 15% by weight, preferably 0 to 10% by weight, particularly preferably 0 to 5% by weight.

The solutions and dispersions of the polymers according to the invention can be converted into powder form by various drying processes such as, for example, spray drying, fluidized spray drying, drum drying or freeze drying. Spray drying is preferably employed as drying process. An aqueous solution or dispersion can be prepared again by dissolving or redispersing the dry polymer powder obtained in this way in water. The conversion into powder form has the advantage of better storability, simpler transportability and less tendency to microbial attack.

In place of the steam-distilled polymer solutions, it is also possible to convert the alcoholic polymer solutions directly into powder form.

The water-soluble or water-dispersible polymers according to the invention are outstandingly suitable for producing soft capsules, in particular for pharmaceutical dosage forms.

The polymers according to the invention produced by free-radical polymerization of vinyl esters and, where appropriate, one or more polymerizable monomers in the presence of polyether-containing compounds and subsequent at least partial hydrolysis of the ester functions of the original vinyl esters are suitable for producing soft capsules.

The polymers can be produced with high reproducibility in the abovementioned processes. No materials of animal origin are used to produce them and, since no vegetable materials are employed either, the problem of products of genetic engineering origin does not arise.

The polymers are not particularly microbiologically susceptible because they do not represent good nutrient media for microbes. The polymer chains are not degraded either by enzymes or by hydrolysis. The preparation of solutions to produce films and for encapsulation is therefore no problem either.

The particular suitability of the described polymers for producing soft capsules derives from their flexibility and softness. This great flexibility usually means that it is unnecessary to employ low molecular weight plasticizers. Thus no change in the shell and the capsule contents occurs because of migration either.

Typical packaged materials are preferably pharmaceutical products such as solid and liquid active ingredients, but also vitamins, carotenoids, minerals, trace elements, food supplements, spices and sweeteners. The capsules can also be used for cosmetic active ingredients (personal care), such as, for example, hair and skin formulations, for oils, perfumes, bath additives or proteins. Further applications in the personal care sector, and further applications for water-soluble packagings are mentioned in WO 99/40156.

Further possible examples of such packaged materials are cleaners, such as soaps, detergents, colorants and bleaches, agrochemicals such as fertilizers (or combinations thereof), crop protection agents such as herbicides, fungicides or pesticides, and seeds.

It is possible in general to use the polymers according to the invention to package contents which are to be protected before they are brought into a wet environment.

TABLE 1

Flexibility of polymers (23° C./54% r.h.)

| Composition | Elongation at break |
|---|---|
| PEG 6 000/polyvinyl acetate (15:85), hydrolyzed | 121% |
| PEG 6 000/polyvinyl acetate 10:90 | 140% |
| PEG 6 000/polyvinyl acetate 5:95 | 209% |

The determination took place on pieces of film in a tensile tester (Texture Analyzer TA.XT 2; Winopal Forschungsbedarf GmbH, 30161 Hannover) in accordance with DIN 53504.

Surprisingly, the flexibility changes only slightly when the ambient humidity changes. This means that on storage in a dry environment the soft capsules do not become brittle and retain their mechanical stability.

TABLE 2

Flexibility of polymers at different ambient humidities (23° C.)

| | Elongations at break [%] at various rel. humidities | | | | |
|---|---|---|---|---|---|
| | 11% | 33% | 54% | 65% | 75% |
| PEG 6 000/polyvinyl acetate (15:85), hydrolyzed | 107 | 113 | 115 | 108 | 103 |
| Polyvinyl alcohol (Mowiol 4/88) | 4 | 40 | 106 | — | — |
| Gelatin 200 Bloom | 0 | — | 0 | — | — |
| Gelatin 200 Bloom + 5% glycerol | 3 | — | 5 | — | — |
| Gelatin 200 Bloom + 35% glycerol | 31 | — | 157 | — | — |

The elasticity is retained even on encapsulation of substances with high hygroscopicity. The polymers are therefore particularly suitable for encapsulating water-sensitive substances.

The rate of dissolution of the polymers according to the invention and soft capsules produced therefrom is extremely high and markedly exceeds that of gelatin and polyvinyl alcohol. In addition, the polymers are soluble in cold water. Gelatin and polyvinyl alcohol dissolve only at higher temperatures. Since many drugs are intended to act quickly after intake, this dissolving behavior is a clear advantage in particular for this use.

TABLE 3

Rate of dissolution of polymers

| Product | 0.08 N HCl | Buffer pH 6.8 |
| --- | --- | --- |
| PEG 6 000/polyvinyl acetate (15:85), hydrolyzed | 58 s | 1 min 00 s |
| Gelatin 200 Bloom + 35% glycerol | 1 min 20 | 1 min 31 |
| (Hydroxypropylmethylcellulose) Pharmacoat 606 | 6 min 21 s | 6 min 31 s |
| Polyvinyl alcohol (Mowiol 8/88) | 3 min 10 s | 3 min 18 s |

The rate of dissolution was determined in a release apparatus (Pharmatest PTS) complying with USP 23 using a film 100 μm thick clamped into a slide frame with an aperture of 3.5×2.5 cm, at 50 rpm and 37° C. The time in which the piece of film has dissolved is indicated.

In contrast to gelatin, it is also possible to encapsulate in the shells according to the invention substances prone to interactions, such as, for example, aldehydes or multiply charged cations. No crosslinking or slowing of the rate of dissolution is evident.

Soft capsules of the composition according to the invention can be coated extremely well using aqueous polymer solutions or polymer suspensions. Thus, a coating which is resistant to gastric fluid and adheres strongly to the surface and, moreover, is stable on storage can be applied by spraying on Kollicoat MAE 30 DP (USP type C methacrylic acid copolymer) in a horizontal drum coater.

To achieve resistance to gastric fluid it is additionally possible for the shell to contain from 20 to 80%, preferably 30 to 70%, of a polymer resistant to gastric fluid.

It is possible to add to the polymers structure-improving auxiliaries in order to modify the mechanical properties such as flexibility and strength. These structure-improving auxiliaries can be divided into 2 large groups.

A) Polymers with a molecular weight greater than 50000, preferably greater than 100000

B) substances which lead to crosslinking of the polymer chains, either of the polymers or of the substances mentioned under A), preferably aldehydes, boric acid and its salts, and, where appropriate, substances which lead to crosslinking of the polymer chains of the structure-improving auxiliaries, preferably alkaline earth metal ions, amines, tannins, and aldehydes and borates.

High molecular weight polymers which can be employed are substances from the following classes:

Polyamino acids such as gelatin, zein, soybean protein and derivatives thereof,
polysaccharides such as starch, degraded starch, maltodextrins, carboxymethylstarch, cellulose, hydroxypropylmethylcellulose, hydroxypropylcellulose, hydroxyethylcellulose, methylcellulose, carboxymethylcellulose, ethylcellulose, cellulose acetate, cellulose acetate phthalate, hydroxypropylcellulose acetate phthalate, hydroxypropylcellulose acetate succinate, hemicellulose, galactomannans, pectins, alginates, carrageenans, xanthan, gellan, dextran, curdlan, pullulan, chitin, and derivatives thereof, synthetic polymers such as polyacrylic acid, polymethacrylic acid, copolymers of acrylic esters and methacrylic esters, polyvinyl alcohols, polyvinyl acetate, polyethylene glycols, polyoxyethylene/polyoxypropylene block copolymers, polyvinylpyrrolidones and derivatives thereof.

These high molecular weight polymers form a network with the polymers and thus increase the strength of the soft capsules. The flexibility is usually not compromised as long as the concentrations used are not very high. Surprisingly, not only water-soluble but also water-insoluble polymers such as copolymers of acrylic esters and methacrylic esters are suitable for this purpose. The capsules still disintegrate as long as the concentration of these water-insoluble polymers remains below 50%.

Substances which lead to crosslinking either of the polymer chains of the polymers or of the added high molecular weight polymers act in a similar way.

Besides the components mentioned, it is possible for the soft capsules according to the invention to contain other conventional constituents. These include fillers, release agents, flow aids, stabilizers and water-soluble or water-insoluble dyes, flavorings and sweeteners.

Examples of dyes are iron oxides, titanium dioxide, which are added in an amount of about 0.001 to 10, preferably of 0.5 to 3, % by weight, triphenylmethane dyes, azo dyes, quinoline dyes, indigo dyes, carotenoids, in order to color the capsules, opacifying agents such as titanium dioxide or talc in order to decrease the transparency and save on dyes.

Flavorings and sweeteners are particularly important when an unpleasant odor or taste is to be masked and the capsule is chewed.

Preservatives are usually unnecessary.

Examples of fillers are inorganic fillers such as oxides of magnesium, aluminum, silicon, titanium or calcium carbonate. The preferred concentration range for the fillers is about 1 to 50% by weight, particularly preferably 2 to 30% by weight, based on the total weight of all the components.

Lubricants are stearates of aluminum, calcium, magnesium and tin, and magnesium silicate, silicones and the like. The preferred concentration range is about 0.1 to 5% by weight, particularly preferably about 0.1 to 3% by weight, based on the total weight of all the components.

Examples of flow aids are fine-particle or extremely fine-particle silicas, modified where appropriate. The preferred concentration range is 0.05 to 3% by weight, particularly preferably 0.1 to 1% by weight, based on the total weight of all the components.

The incorporation of active ingredients into the shell represents a special case. This may be advantageous for separating incompatible active ingredients from one another. The active ingredient with the smallest dose should then be incorporated into the shell.

The shell of the packaging materials according to the invention consists of 10 to 100%, preferably 20 to 98%, polymers, where appropriate 0 to 80%, preferably 1 to 50%, structure-improving auxiliaries and, where appropriate, 0 to 30%, preferably 0.1 to 30%, other conventional constituents.

The packaging materials are produced by conventional processes, for example the rotary die process, the Accogel process, the Norton process, the drop or blow process or by the Colton-Upjohn process. These processes are described in W. Fahrig and U. Hofer, Die Kapsel, Wissenschaftliche Verlagsgesellschaft mbH Stuttgart, 1983.

Method for Preparing the Polymers

The polyether-containing compound is introduced into a polymerization vessel and heated to 80° C. with stirring under a gentle stream of nitrogen. Vinyl acetate and the other monomer are metered in with stirring over the course of 3 h.

Simultaneously, a solution of 1.4 g of tert-butyl perpivalate in 30 g of methanol is added, likewise over the course of 3 h. The mixture is then stirred at 80° C. for 2 h. After cooling, the polymer is dissolved in 450 ml of methanol. For the hydrolysis, 50 ml of a 10% strength methanolic sodium hydroxide solution are added at 30° C. After about 40 min, the reaction is stopped by adding 750 ml of 1% strength acetic acid. The methanol is removed by distillation.

The K values were determined on 1% solutions in N-methylpyrrolidone.

TABLE 4

| Example | Grafting base | Vinyl ester | Comonomer | K value | Degree of hydrolysis [%] |
|---|---|---|---|---|---|
| 1 | PEG 1500[1] 72 g | Vinyl acetate, 410 g | — | 47 | >95 |
| 2 | PEG 4000 72 g | Vinyl acetate, 410 g | — | 51 | >95 |
| 3 | PEG 6000, 72 g | Vinyl acetate, 410 g | — | 54 | >95 |
| 4 | PEG 6000, 137 g | Vinyl acetate, 410 g | — | 49 | >95 |
| 5 | PEG 6000, 22 g | Vinyl acetate 410 g | — | 73 | >95 |
| 6 | PEG 6000, 410 g | Vinyl acetate 410 g | — | 42 | >95 |
| 7 | PEG 9000, 137 g | Vinyl acetate, 410 g | — | 58 | >95 |
| 8 | Polyglycerol 2200, 72 g | Vinyl acetate, 410 g | — | 66 | >95 |
| 9 | PEG-PPG block copolymer 8000[2], 72 g | Vinyl acetate, 410 g | — | 45 | >95 |
| 10 | Methylpolyethylene glycol 2000[3] 72 g | Vinyl acetate, 410 g | — | 47 | >95 |
| 11 | Alkylpolyethylene glycol 3500[4] 72 g | Vinyl acetate, 410 g | — | 48 | >95 |
| 12 | PPG 4000[5] 72 | Vinyl acetate 410 g | — | 50 | >95 |
| 13 | PEG 20000 72 g | Vinyl acetate, 410 g | — | 69 | >95 |
| 14 | PEG 20000 103 g | Vinyl acetate, 410 g | — | 64 | >95 |
| 15 | PEG 20000 137 g | Vinyl acetate, 410 g | — | 59 | >95 |
| 16 | PEG 20000 615 g | Vinyl acetate 410 g | — | 55 | 86 |
| 17 | PEG 35000 72 g | Vinyl acetate, 410 g | — | 77 | >95 |
| 18 | PEG 35000 137 g | Vinyl acetate, 410 g | — | 80 | >95 |
| 19 | PEG 35000 205 g | Vinyl acetate 410 g | — | 65 | 97 |
| 20 | Dimethicone copolyol[6], 202 g | Vinyl acetate 410 g | — | 58 | >95 |
| 21 | Poly(sodium methacrylate-co-methylpoly-ethylene glycol methacrylate)[7] 103 g, | Vinyl acetate 410 g | — | 43 | >95 |
| 22 | ethoxylated polyethyleneimine[8] | Vinyl acetate, 410 g | — | 52 | >95 |

TABLE 4-continued

| Example | Grafting base | Vinyl ester | Comonomer | K value | Degree of hydrolysis [%] |
|---|---|---|---|---|---|
| 23 | PEG 6000, 72 g | Vinyl acetate, 386 g | Methyl methacrylate, 24 g | 47 | >95 |
| 24 | PEG 20000, 72 g | Vinyl acetate 328 g | N-Vinyl-pyrrolidone, 82 g | 61 | >95 |
| 25 | PEG 20000, 72 g | Vinyl acetate 362 g | 3-Methyl-1-vinylimidazolium methyl sulfate, 48 g | 53 | >95 |
| 26 | PEG 6000, 72 g | Vinyl acetate 367 g | N-Vinyl-formamide, 41 g | 57 | >95 |
| 27 | PEG 6000, 72 g | Vinyl acetate, 326 g | N-Vinyl-formamide, 82 g | 67 | >95 |
| 28 | PEG 35000, 270 g | Vinyl acetate, 410 g |  | 59 | 96 |
| 29 | PEG 35000, 270 g | Vinyl acetate, 410 g | Pentaerythritol triallyl ether, 1.6 g | 71 | 95 |
| 30 | PEG 35000, 270 g | Vinyl acetate, 410 g | Pentaerythritol trially ether, 0.8 g | 65 | 94 |
| 31 | PEG 35000, 270 g | Vinyl acetate, 410 g | N,N'-Divinyl-ethyleneurea 0.7 g | 73 | 95 |
| 32 | PEG 35000, 270 g | Vinyl acetate, 410 g | Pentaerythritol triallyl ether, 1.6 g | 50 | 94 |

[1]PEG x: Polyethylene glycol with average molecular weight x
[2]Lutrol F 68 supplied by BASF Aktiengesellschaft (PPG: polypropylene glycol)
[3]Pluriol A 2000 E supplied by BASF Aktiengegellschaft
[4]Lutensol AT 80 supplied by BASF Aktiengesellschaft ($C_{16}$–$C_{18}$-fatty alcohol + 80 EO)
[5]Polypropylene glycol with average molecular weight 4000
[6]Belsil DMC 6031TM supplied by Wacker Chemie GmbH
[7]Sodium methacrylate/methylpolyethylene glycol methacrylate molar ratio 4:1; methylpolyethylene glycol with molecular weight about 1000
[8]Prepared from 12.5% polyethyleneimine (average molecular weight 1400) and 87.3% ethylene oxide

EXAMPLE 33
Reaction with 3-chloro-2-hydroxypropyltrimethylammonium Chloride 22 g of a 60% strength aqueous solution of 3-chloro-2-hydroxypropyltrimethylammonium chloride and 3.5 g of sodium hydroxide are added to 400 g of a 32.9% strength solution from Example 3. The mixture is stirred at 60° C. for 3 hours and then at 90° C. for a further two hours. A clear solution is obtained.

EXAMPLE 34
Reaction with 3-chloro-2-hydroxypropyltrimethylammonium Chloride 46 g of a 60% strength aqueous solution of 3-chloro-2-hydroxypropyltrimethylammonium chloride and 6 g of sodium hydroxide are added to 400 g of a 15.3% strength solution from Example 26. The mixture is stirred at 60° C. for 3 hours and then at 90° C. for a further two hours. A clear solution is obtained.

EXAMPLE 35
Subsequent Crosslinking with Borax

A 5% strength aqueous solution of disodium tetraborate (borax) is added to a stirred 19.3% strength aqueous solution of the polymer from Example 28 at room temperature over the course of half an hour. An increase in viscosity is observed.

| Amount of 5% borax solution added [g] | Brookfield viscosity (LVF, Spindle 2, 30 rpm, 23° C.) [mPas] |
|---|---|
| 0 | 110 |
| 14.9 | 128 |
| 18.0 | 216 |
| 21.0 | 534 |
| 24.0 | 2228 |
| 26.9 | 7520[1] |
| 29.8 | 29190[2] |

[1]Spindle 4, 30 rpm
[2]Spindle 4, 6 rpm

EXAMPLE 36

1.0 kg of polymer of polyethylene glycol 6000/polyvinyl acetate (15:85) hydrolyzed, was dissolved in 1.5 kg of demineralized water, and the solution was heated to 60° C. and drawn out to a film 300 μm thick, and dried at 60° C. Soft capsules filled with vitamin E (2 parts) and medium chain-length triglycerides (8 parts) were produced from this film by the rotary die process. The capsules were then dried at 35° C. in a fluidized bed.

The dissolution time in simulated gastric fluid was 2 min 30 s. During storage at 11% r.h. the capsules retained their flexibility and disintegration properties.

EXAMPLE 37

0.66 kg of polymer of polyethylene glycol 6000/polyvinyl acetate (15/85) hydrolyzed, 0.04 kg of pectin and 0.16 kg of polyvinyl alcohol (Mowiol 4/88) were dissolved with heating in 1.58 kg of demineralized water. A pigment suspension was prepared from 16 g of red iron oxide (Sicovit red 30, BASF Aktiengesellschaft) and 33 g of titanium dioxide with 115 g of demineralized water and, after homogenization in a corundum disk mill, added to the polymer solution with stirring. The suspension was drawn out to a film 400 μm thick. Soft capsules filled with ibuprofen (3 parts) and medium chain-length triglycerides (7 parts) were produced From this film by the rotary die process. The capsules were then dried at 35° C. in a fluidized bed.

The dissolution time of the capsules in simulated gastric fluid was 3 min 03 s. During storage at 11% r.h. for 3 months, the capsules retained their flexibility and disintegration properties.

EXAMPLE 38

0.6 kg of polymer of polyethylene glycol 6000/polyvinyl acetate (15/85) hydrolyzed, 0.5 kg of gelatin 200 Bloom and 10 g of 10% beta-carotene dry powder (Lucarotin 10% CWD) were dissolved with heating in 1.4 kg of demineralized water and 0.10 kg of glycerol. The solution was drawn out to a film 400 μm thick.

Soft capsules filled with ibuprofen (3 parts) and medium chain-length triglycerides (7 parts) were produced from this film by the rotary die process. The capsules were then dried at 35° C. in a fluidized bed.

The dissolution time of the capsules in simulated gastric fluid was 4 min 30 s.

EXAMPLE 39

0.175 kg of a copolymer of methacrylic acid and ethyl acrylate (Kollicoat MAE 100 P) was dispersed in 1.625 kg of water and adjusted to pH 6.5 by adding 20% strength sodium hydroxide solution with stirring. Then 0.7 kg of polymer of methylpolyethylene glycol 6000/polyvinyl acetate (15/85) hydrolyzed was dissolved with stirring. This solution was drawn out to a film 350 μm thick.

Soft capsules filled with verapamil HCl (3 parts), Cremophor RH 40 (1 part) and medium chain-length triglycerides (6 parts) were produced from this film by the rotary die process. The capsules were then dried at 35° C. in a fluidized bed.

The dissolution time of the capsules in simulated gastric fluid was 3 min 45 s.

EXAMPLE 40

0.95 kg of polymer of polyethylene glycol 6000/polyvinyl acetate (15/85) hydrolyzed, 0.1 kg of hydroxypropylmethylcellulose (Pharmacoat 606), 0.05 kg of carrageenan and 10 g of 10% beta-carotene dry powder (Lucarotin 10% CWD) and 0.1 kg of polyethylene glycol 6000 were dissolved with heating in 1.4 kg of demineralized water. The solution was drawn out to a film 350 μm thick.

Soft capsules filled with theophylline (3 parts), polysorbate 80 (0.5 part) and medium chain-length triglycerides (6 parts) were produced from this film by the Accogel process by dimpling the film, injecting the filling and closing with a second film. The capsules were then dried at 35° C. in a fluidized bed.

The dissolution time of the capsules in simulated gastric fluid was 2 min 55 s. No embrittlement was detectable even on storage at 11% ambient humidity.

EXAMPLE 41

1.0 kg of polymer of polyethylene glycol 6000/polyvinyl acetate (15/85) hydrolyzed was dissolved in 2.3 kg of demineralized water, and 10 g of sodium tetraborate were added. The solution was drawn out to a film 400 μm thick. Soft capsules filled with tocopherol acetate (3 parts), polysorbate 80 (0.5 part) and medium chain-length triglycerides (6.5 parts) were produced from this film by the Accogel process by dimpling the film, injecting the filling and closing with a second film. The capsules were then dried at 35° C. in a fluidized bed. The dissolution time of the capsules in simulated gastric fluid was 4 min 35 s. No embrittlement was detectable even on storage at 11% ambient humidity.

COMPARATIVE EXAMPLE

Soft capsules could not be produced either with gelatin or with polyvinyl alcohol or hydroxypropylmethylcellulose without addition of plasticizer. The films were too brittle and fragile.

We claim:
1. A soft capsule shell comprising
   (a) from 10 to 100% of polymers prepared by polymerization of vinyl esters in the presence of polyethers
   (b) from 0 to 80% of structure-improving auxiliaries and
   (c) from 0 to 30% of other constituents selected from the group consisting of fillers, release agents, flow aids, stabilizers, water-soluble or water-insoluble dyes, flavorings and sweeteners,
and wherein the polymers (a) are obtained by free-radical polymerization of
   a) at least one vinyl ester of $C_1$–$C_{24}$-carboxylic acids in the presence of
   b) polyether-containing compounds of the general formula I

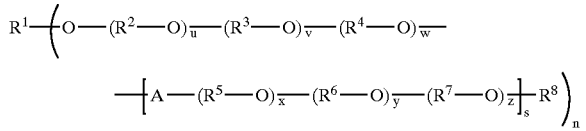

in which the variables have, independently of one another, the following meaning:
   $R^1$ hydrogen, $C_1$–$C_{24}$-alkyl, $R^6$—C(=O)—, $R^6$—NH—C(=O)—, polyalcohol residue;
   $R^5$ hydrogen, $C_1$–$C_{24}$-alkyl, $R^6$—C(=O)—, $R^6$—NH—C(=O)—;
   $R^2$ to $R^4$ —(CH$_2$)$_2$—, —(CH$_2$)$_3$—, —(CH$_2$)$_4$—, —CH$_2$—CH($R^6$)—, —CH$_2$—CHO$R^7$—CH$_2$—;
   $R^6$ $C_1$–$C_{24}$-alkyl;
   $R^7$ hydrogen, $C_1$–$C_{24}$-alkyl, $R^6$—C(=O)—, $R^6$—NH—C(=O)—;
   A —C(=O)—O, —C(=O)—B—C(=O)—O, —C(=O)—NH—B—NH—C(=O)—O;
   B —(CH$_2$)$_t$—, arylene, optionally substituted;
   n 1 to 1000;
   s 0 to 1000;

t 1 to 12;
u 1 to 5000;
v 0 to 5000;
w 0 to 5000;
x 0 to 5000;
y 0 to 5000;
z 0 to 5000; and c) from 0 to 50% of one or more other copolymerizable monomers and subsequent at least partial hydrolysis of the ester functions in the original monomers a).

2. A soft capsule shell as claimed in claim 1, wherein the polyether-containing compounds of formula I have a number average molecular weight of from 300 to 100000, and the variables have, independently of one another, the following meaning:

$R^1$ hydrogen, $C_1$–$C_{12}$-alkyl, $R^6$—C(=O)—, $R^6$—NH—C(=O)—, polyalcohol residue;

$R^5$ hydrogen, $C_1$–$C_{12}$-alkyl, $R^6$—C(=O)—, $R^6$—NH—C(=O)—;

$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ $C_1$–$C_{12}$-alkyl;

$R^7$ hydrogen, $C_1$–$C_{12}$-alkyl, $R^6$—C(=O)—, $R^6$—NH—C(=O)—;

n 1 to 8;
s 0;
u 2 to 2000;
v 0 to 2000;
w 0 to 2000.

3. A soft capsule shell as claimed in claim 1, wherein the polyether-containing compounds of formula I have a number average molecular weight of from 500 to 50000, and the variables have, independently of one another, the following meaning:

$R^1$ hydrogen, $C_1$–$C_6$-alkyl, $R^6$—C(O)—, $R^6$—NH—C(=O)—;

$R^5$ hydrogen, $C_1$–$C_6$-alkyl, $R^6$—C(O)—, $R^6$—NH—C(=O)—;

$R^2$ to $R^4$ —(CH$_2$)$_2$—, —(CH$_2$)$_3$—, —(CH$_2$)$_4$—, —CH$_2$—CH($R^6$)—, —CH$_2$—CHOR$^7$—CH$_2$—;

$R^6$ $C_1$–$C_6$-alkyl;

$R^7$ hydrogen, $C_1$–$C_6$-alkyl, $R^6$—C(=O)—, $R^6$—NH—C(=O)—;

n 1;
s 0;
u 5 to 1000;
v 0 to 1000;
w 0 to 1000.

4. A soft capsule shell as claimed in claim 1, wherein the polymers (a) are obtained by free-radical polymerization of a) at least one vinyl ester of $C_1$–$C_{24}$-carboxylic acids in the presence of b) polyether-containing compounds and c) one or more other copolymerizable monomers and subsequent at least partial hydrolysis of the ester functions in the original monomers a), wherein the polyether-containing compounds b) have been prepared by polymerization of ethylenically unsaturated alkylene oxide-containing monomers, alone or together with other copolymerizable monomers.

5. A soft capsule shell as claimed in claim 4, wherein the polyether-containing compounds b) have been prepared by polymerization of polyalkylene oxide vinyl ethers, alone or together with other copolymerizable monomers.

6. A soft capsule shell as claimed in claim 4, wherein the polyether-containing compounds b) have been prepared by polymerization of polyalkylene oxide (meth)acrylates, alone or together with other copolymerizable monomers.

7. A soft capsule shell as claimed in claim 1, wherein said other copolymerizable monomers c) are selected from the group consisting of:

acrylic acid, methacrylic acid, maleic acid, fumaric acid, crotonic acid, maleic anhydride and its monoesters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylates, 2-hydroxyethyl methacrylate, hydroxypropyl methacrylates, alkylene glycol (meth)acrylates, styrene, unsaturated sulfonic acids.

8. A soft capsule shell as claimed in claim 1, wherein the amounts of a), b) and c) are a) 10 to 98% by weight
b) 2 to 90% by weight
c) 0 to 50% by weight.

9. A soft capsule shell as claimed in claim 1, wherein the amounts of a), b) and c) are a) 50 to 97% by weight
b) 3 to 50% by weight
c) 0 to 20% by weight.

10. A soft capsule shell as claimed in claim 1, wherein the amounts of a), b) and c) are a) 65 to 97% by weight
b) 3 to 35% by weight
c) 0 to 20% by weight.

11. A soft capsule shell as claimed in claim 1, wherein the resulting polymers are subsequently crosslinked.

12. A soft capsule shell as claimed in claim 11, wherein the resulting polymers are subsequently crosslinked by reaction with one or more compounds selected from the group consisting of dialdehydes, diketones, dicarboxylic acids, boric acid, boric acid salts, and salts of multiply charged cations.

13. A soft capsule shell as claimed in claim 1, wherein the structure-improving auxiliaries (b) employed are compounds from the following classes:

a) polymers with a molecular weight of more than 50000,
b) substances leading to crosslinking of the polymer chains of the polymers,
c) and, optionally, substances which lead to crosslinking of the polymer chains of the structure-improving auxiliaries.

14. A soft capsule shell as claimed in claim 1, wherein the structure-improving auxiliaries employed are polymers selected from the group consisting of the following classes of substances: polyamino acids, polysaccharides and synthetic polymers.

15. A soft capsule shell as claimed in claim 1, which consists of from 10 to 100% by weight of polymers of vinyl esters on polyether, from 0 to 80% of structure-improving auxiliaries and from 0 to 30% of said other constituents.

16. A soft capsule shell as claimed in claim 1, obtained by a process selected from the groups consisting of the rotary die process, Accogel process, Norton process, drop or blow process or the Colton-Upjohn process.

17. A soft capsule shell as claimed in claim 1, which encapsulates one or more active pharmaceutical ingredients, vitamins, carotenoids, minerals, trace elements, food supplements, cosmetic active ingredients, crop protection agents, bath additives, perfume, flavoring, cleaners or detergents.

18. A soft capsule shell as claimed in claim 1, wherein the shell comprises from 20 to 80% of a polymer resistant to gastric fluid.

19. A soft capsule shell as claimed in claim 1, wherein resistance to gastric fluid is achieved by applying after production a coating resistant to gastric fluid by pharmaceutical coating processes.

20. A soft capsule shell as claimed in claim 17 which encapsulates one or more pharmaceutical ingredients.

21. A soft capsule shell as claimed in claim 17 which encapsulates one or more cosmetic active ingredients, crop protection agents, for cleaners or food supplements.

22. A soft capsule shell as claimed in claim 14, wherein said polyamino acids are selected from the group consisting of gelatin, zein, soybean protein and derivatives thereof.

23. A soft capsule shell as claimed in claim 14, wherein said polysaccharides are selected from the group consisting of starch, degraded starch, maltodextrins, carboxymethyl starch, cellulose, hydroxypropylmethylcellulose, hydroxypropylcellulose, hydroxyethylcellulose, methylcellulose, carboxymethylcellulose, ethylcellulose, cellulose acetate, cellulose acetate phthalate, hydroxypropylcellulose acetate phthalate, hydroxypropylcellulose acetate succinate, hemicellulose, galactomannans, pectins, alginates, carrageenans, xanthan, gellan, dextran, curdlan, pullulan, gum arabic, chitin, and derivatives thereof.

24. A soft capsule shell as claimed in claim 14, wherein said synthetic polymers are selected from the group consisting of polyacrylic acid, polymethacrylic acid, copolymers of acrylic esters and methacrylic esters, polyvinyl alcohols, polyvinyl acetate, polyethylene glycols, polyoxyethylene/polyoxypropylene block copolymers, polyvinylpyrrolidones and derivatives thereof.

25. A soft capsule shell as claimed in claim 1, wherein the amounts of (a), (b) and (c) are:

(a) 20 to 98% by weight;

(b) 1 to 50% by weight; and (c) 0.1 to 30% by weight.

* * * * *